(12) United States Patent
von Hoffmann et al.

(10) Patent No.: US 8,012,191 B2
(45) Date of Patent: Sep. 6, 2011

(54) THERAPEUTIC PACK

(75) Inventors: Kristen L. von Hoffmann, Montclair, NJ (US); Eric W. von Hoffmann, Montclair, NJ (US); Diana von Hoffmann, Montclair, NJ (US)

(73) Assignee: Hometown Sports, LLC, Montclair, NJ (US)

( * ) Notice: Subject to any disclaimer, the term of this patent is extended or adjusted under 35 U.S.C. 154(b) by 1291 days.

(21) Appl. No.: 11/610,712

(22) Filed: Dec. 14, 2006

(65) Prior Publication Data
US 2007/0083251 A1    Apr. 12, 2007

Related U.S. Application Data

(63) Continuation-in-part of application No. 10/193,778, filed on Jul. 12, 2002, now abandoned, and a continuation-in-part of application No. 10/389,862, filed on Mar. 14, 2003, now abandoned.

(51) Int. Cl.
*A61F 7/00* (2006.01)
*A61F 7/10* (2006.01)

(52) U.S. Cl. .......................................... 607/114; 607/96

(58) Field of Classification Search .................. 607/96, 607/114, 108–112
See application file for complete search history.

(56) References Cited

U.S. PATENT DOCUMENTS

| | | |
|---|---|---|
| 3,596,713 A | 8/1971 | Katz |
| 4,044,773 A | 8/1977 | Baldwin, III |
| 4,104,883 A | 8/1978 | Naef |
| 4,327,447 A | 5/1982 | Carnaghi et al. |
| 4,381,025 A * | 4/1983 | Schooley ........................ 607/112 |
| 4,505,201 A | 3/1985 | Abele |
| 4,516,564 A | 5/1985 | Koiso et al. |
| 4,530,220 A | 7/1985 | Nambu et al. |
| 4,596,250 A | 6/1986 | Beisang, III et al. |
| 4,628,932 A | 12/1986 | Tampa |
| 4,648,864 A | 3/1987 | Evans et al. |
| 4,731,283 A | 3/1988 | Sakane et al. |
| 4,736,088 A | 4/1988 | Bart |
| 4,973,647 A | 11/1990 | Bretches et al. |
| 4,981,135 A | 1/1991 | Hardy |
| 5,040,557 A | 8/1991 | Morgan |

(Continued)

FOREIGN PATENT DOCUMENTS
EP    0360931 A    4/1990
(Continued)

OTHER PUBLICATIONS

Website of Wikipedia, The Free Encyclopedia: http://en.wikipedia.org/wiki/basic_knitted_fabrics, "Basic Knitted Fabrics".

(Continued)

*Primary Examiner* — John P Leubecker
(74) *Attorney, Agent, or Firm* — Christopher Paradies; Fowler White Boggs P.A.

(57) ABSTRACT

A therapeutic pack provides effective therapeutic heating or cooling to an area of a body. The therapeutic pack comprises a fabric bag and a plurality of therapeutic modules within the bag. The bag consists of taffeta or a spandex such that the bag drapes. The therapeutic modules are capable of freely moving within the bag relative to one another. The therapeutic modules may include a material that repeatedly provides a prolonged cooling or heating, such as a phase change material.

17 Claims, 3 Drawing Sheets

U.S. PATENT DOCUMENTS

| | | | |
|---|---|---|---|
| 5,069,208 A | | 12/1991 | Noppel et al. |
| 5,190,033 A | | 3/1993 | Johnson |
| 5,216,900 A | * | 6/1993 | Jones .......................... 62/457.2 |
| 5,275,156 A | | 1/1994 | Milligan et al. |
| 5,314,005 A | | 5/1994 | Dobry |
| 5,534,020 A | | 7/1996 | Cheney, III et al. |
| 5,603,727 A | | 2/1997 | Clark et al. |
| 5,628,772 A | | 5/1997 | Russell |
| 5,697,961 A | | 12/1997 | Kiamil |
| 5,709,945 A | | 1/1998 | Lee et al. |
| 5,887,296 A | * | 3/1999 | Handwerker ..................... 4/498 |
| 5,984,953 A | | 11/1999 | Sabin et al. |
| 6,099,555 A | | 8/2000 | Sabin |
| 6,438,755 B1 | | 8/2002 | MacDonald et al. |
| 6,610,084 B1 | | 8/2003 | Torres |
| 6,855,422 B2 | * | 2/2005 | Magill et al. .................. 428/373 |
| 6,916,334 B2 | | 7/2005 | Noonan |
| 7,060,086 B2 | | 6/2006 | Wilson et al. |
| 7,065,983 B2 | * | 6/2006 | Trinh et al. ..................... 62/530 |
| 7,291,164 B2 | * | 11/2007 | Peterman et al. ............. 607/108 |
| 7,396,044 B2 | * | 7/2008 | Bauer et al. ................. 280/743.2 |
| 2001/0006865 A1 | | 7/2001 | Holman |
| 2003/0055475 A1 | | 3/2003 | Rousmaniere |
| 2003/0124278 A1 | | 7/2003 | Clark et al. |
| 2004/0210288 A1 | | 10/2004 | Karapetyan |
| 2005/0143544 A1 | * | 6/2005 | Husemann et al. ............ 526/319 |
| 2007/0055330 A1 | | 3/2007 | Rutherford |

FOREIGN PATENT DOCUMENTS

| | | |
|---|---|---|
| GB | 2226956 A | 7/1990 |
| GB | 2316318 A | 2/1998 |
| GB | 2333708 A | 8/1999 |
| JP | 08-084743 A | 4/1996 |
| KR | 20-0397467 Y1 | 10/2005 |

OTHER PUBLICATIONS

Website of IB Sports, LLC, Westerville, Ohio: http://www.icebeams.com/ad%20fabrics.htm, "Fabrics".

TEAP Energy, Encapsulation Methods, 1 page, http://www.teappcm.comencapsulation.html. This NPL reference was submitted in the parent U.S. Appl. No. 10/389,862, Mar. 5, 2003.

TEAP Energy, PCM Filled Spheres, Mar. 5, 2003, 2 pages, http://www.mjm-engineering.com/spheres.html. This NPL reference was submitted in the parent U.S. Appl. No. 10/389,862.

American Health Products, Freezer Storage Bags, 3 pages, www.ahpc.com. This NPL reference was submitted in the parent U.S. Appl. No. 10/389,862.

International Search Report dated Sep. 17, 2009, for corresponding International Application PCT/US2009/031439, 3 pages.

Fabric / Define Fabric at Dictionary.com downloaded from http://dictionary.reference.com/browse/fabric on Nov. 30, 2010, 2 pages.

Plastic film / Define Plastic film at Dictionary.com downloaded from http://dictionary.reference.com/browse/plastic+film?&qsrc= on Nov. 30, 2010, 1 page.

* cited by examiner

US 8,012,191 B2

THERAPEUTIC PACK

RELATED APPLICATIONS

The present application is a continuation-in-part application of U.S. patent application Ser. No. 10/193,778, filed on Jul. 12, 2002, now abandoned and a continuation-in-part application of U.S. patent application Ser. No. 10/389,862, filed on Mar. 14, 2003, now pending.

FIELD OF THE INVENTION

The field relates to therapeutic packs, for example, therapeutic packs, used for cooling or heating an area to be subjected to a therapeutic treatment, such as an injured area of a human body.

BACKGROUND OF THE INVENTION

Conventional therapeutic packs may be used to provide a therapeutic treatment to an area of a living body to be subject to a cold or heat treatment. For example, therapeutic packs may be used to treat sports related injuries, by providing a cooling or heating temperature to the injured area.

It is believed that U.S. Pat. No. 4,044,773, which is expressly incorporated herein by reference, refers to a cold therapeutic package, in which water is sealed within an interior of a thin polyurethane bladder. The water is then frozen, resulting in the formation of a thin layer of ice within the bladder. After being exposed to a deforming force, such as a rolling or striking force, the layer of ice is divided into a plurality of small ice particles. These small ice particles may move at least substantially freely relative to one another when the cold therapeutic package is applied to an area to be subjected to a cold treatment, thereby promoting easier application of the cold package to the area. However, the thick materials of conventional cold pack bags do not conform readily to the complex, reentrant curves of the human body, because the bags must prevent leakage of water or other cooling medium.

SUMMARY OF THE INVENTION

It is an object of the present invention to improve conventional therapeutic packs by providing a pack design that promotes the cooling or heating effects of the therapeutic pack and better conforms to an area to be subjected to a therapeutic treatment.

It is another object of the present invention to provide a therapeutic pack, which is better suited to provide a cooling or heating temperature to an area to be subjected to a therapeutic treatment.

It is another object of the present invention to provide a therapeutic pack, which does not require a substantial initial deforming force for subdividing a cooling medium, such as ice, into a plurality of smaller particles.

To achieve these objects, an exemplary therapeutic pack according to the present invention includes a container, also referred to herein as a bag, having an interior space and a plurality of therapeutic modules situated in the interior space of the container, in which the therapeutic modules move freely, or at least substantially freely, relative to one another without the need for a substantial initial deforming force.

In this manner, it is believed that the various exemplary therapeutic packs of the present invention may better treat an injury of a living body, for example, a sports related injury of a human body. It is also believed that the therapeutic packs of the present invention provide an advantageous solution for treating injuries in large scale treatment centers, such as hospitals.

One advantage of a fabric bag made of a taffeta or spandex is that the user does not feel the initial shock of cold typically associated with plastic even when the bag is directly placed against bare/sensitive skin. Another advantage of the therapeutic pack is that the system prevents frost bite, unlike plastic packs which require an additional fabric such as a towel to prevent frost bite or injury to the skin. The modules may provide sustained cooling or heating in a temperature range based on the phase change temperature of the phase change material and the wall thickness of the modules while the thin fabric provides ready transfer of heat to or from the modules. An additional advantage is that the bag drapes on the body providing an even distribution of cooling therapy to regular and irregular body surfaces. Yet another advantage of the spandex fabric is that the stretchable material better conforms to the body even when the bag is full of therapeutic modules. Still another advantage of a lightweight spandex is that the bag not only conforms and remains in place without slipping but also grips the body part holding the bag in place. Also, the fabric does not sweat as plastic surfaces do and remains dry to the touch even during therapy.

DETAILED DESCRIPTION

The examples described and the drawings rendered are illustrative and are not to be read as limiting the scope of the invention as it is defined by the appended claims.

Figure 1:
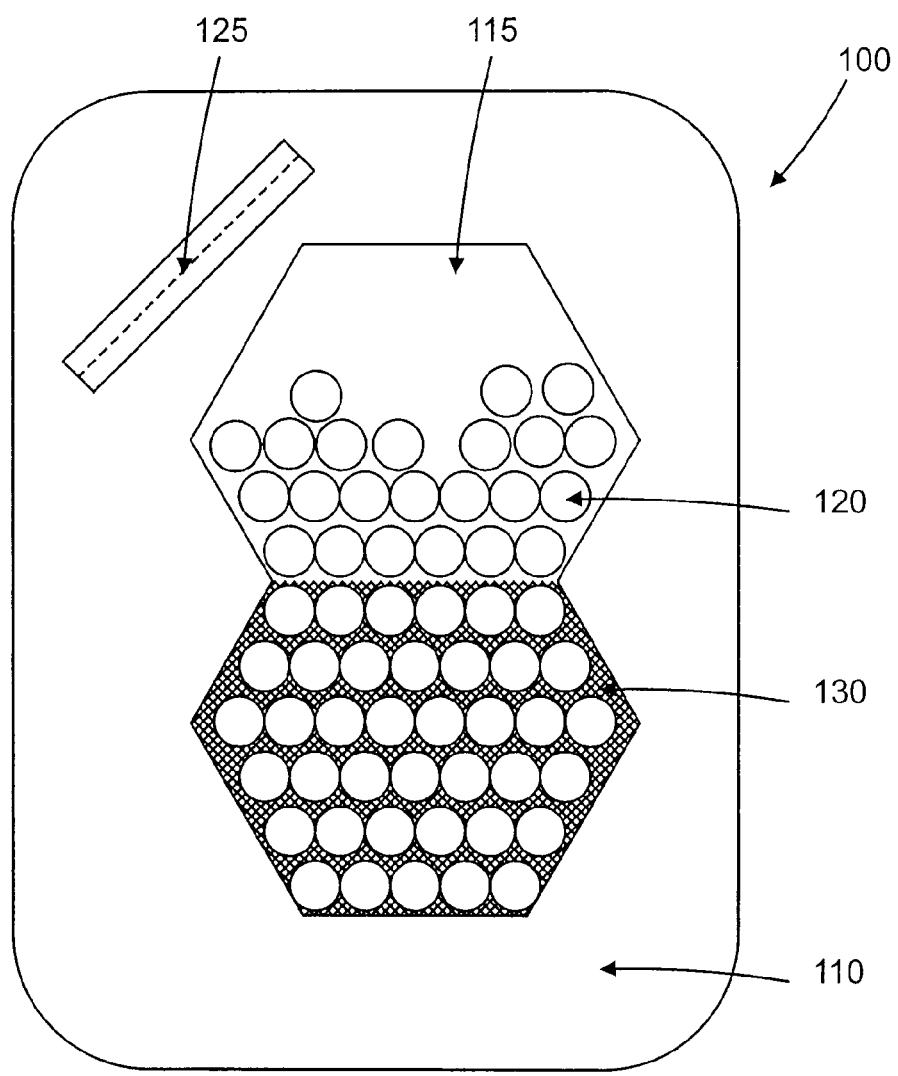
FIG. 1 is a cut-away view showing a first exemplary therapeutic pack.

Referring now to FIG. 1, there is seen a cut-away view of a first exemplary therapeutic pack 100 according to the present invention. As shown in FIG. 1, the therapeutic pack 100 includes a bag 110 having an interior space 115 and a plurality of therapeutic modules 120 situated within the interior space 115 of the bag 110. For example, the bag 110 may include more than 1000 spherical therapeutic modules 120. In one specific embodiment, each spherical therapeutic module has a diameter of between about 11/32 inches and 13/32 inches and each weighing, for example, between about 0.4 grams and 0.6 grams. A volume less than one cubic inch, more preferably less than 0.4 cubic inches is preferred for each module, allowing many modules to conform directly to the body surface. The bag 110 may weigh, for example, about 454 grams when filled with the therapeutic modules 120, depending on the size of the bag and number and volume of therapeutic modules within. An anti-microbial agent may be incorporated in the module shell of the therapeutic modules 120.

The bag 110 may be made of a strong, durable material and should have a suitable thickness, such that the bag 110 conforms to the area to be subjected to a therapeutic treatment. For example, the material of the bag 110 may have a thickness of less than four thousandths of an inch, for example, approximately three and one half thousandths of an inch (i.e., 3½ mil). For example, a fabric of a taffeta or a spandex, such as a nylon taffeta, polyester taffeta, polyester/nylon taffeta and a nylon-treco spandex may be used to form bag 110.

It is believed that the use of nylon taffeta in bag 110 is advantageous, since taffeta is less likely to irritate and/or burn the area to be subjected to a therapeutic treatment. It is also believed that taffeta exhibits good conductive properties for conducting the cooling or heating temperature to the area to be subjected to a therapeutic treatment, without causing an ice burn, for example.

Additionally, the bag 110 may include an antimicrobial and/or antifungal agent to prevent infection. For example, this may reduce the chance of introducing an infectious organism, if the area to be subjected to a temperature treatment includes an open cut and/or abrasion on a human body part. In one embodiment, an antifungal and antimicrobial agent permeates a polyester taffeta bag.

Furthermore, the bag 110 may be designed in any shape, such as oval, square, rectangular, etc. For example, the bag 110 may include a substantially rectangular bag dimensioned, for example, about 6½ inches by 9 inches, having a thickness of about 1¼ inches, when filled with therapeutic modules 120 and laid flat.

The bag 110 may permanently enclose the therapeutic modules 120 (i.e., the bag 110 may be a permanently sealed unit) or, as shown in FIG. 1, the bag 110 may include an access apparatus 125, such as a zipper, hook-and-loop tape (e.g. Velcro®), buttons, straps, a twist tie, a slide-lock (e.g. Ziplock®) and/or snaps, operable to permit access to the interior space 115 of the bag 110. In this manner, the therapeutic modules 120 may be replaced if necessary.

In one specific embodiment, the bag 110 is a polyester taffeta. In an alternative embodiment, the polyester taffeta is lined with a high density polyethylene thin film or some other water impermeable lining. Unlike stiffer materials, polyester taffeta drapes, as that term is used in the fashion industry, meaning that the material easily conforms to the human form under its weight.

The interior space 115 of the bag 110 between the therapeutic modules 120 may remain devoid of any material, or may include, for example, a filling medium 130, as shown in FIG. 1. The filling medium 130 may include, for example, a gas, such as air or dessicated air, a gelatinous material, a material resistant to expansion when heated (e.g. above 20° C.), a material resistant to freezing when cooled (e.g. below 0° C.) or a chemical substance that generates heat or cold by a chemical reaction or a phase change, for example, without the need for an external cooling or heating source, such as a freezer or heater.

It should be noted that the interior space 115 of the bag 110 between the temperature modules 120 may be completely filled with the filling medium 130 or, alternatively, may only be partially filled with the filling medium 130. In this manner, the bag 110 may permit the filling medium 130 to expand within the bag 110 while freezing or heating, without rupturing the bag 110. Alternatively, each shell 205, as shown in FIG. 2, may enclose less than its full volume of a therapeutic medium 210, allowing for expansion of the therapeutic medium 210.

Figure 2:
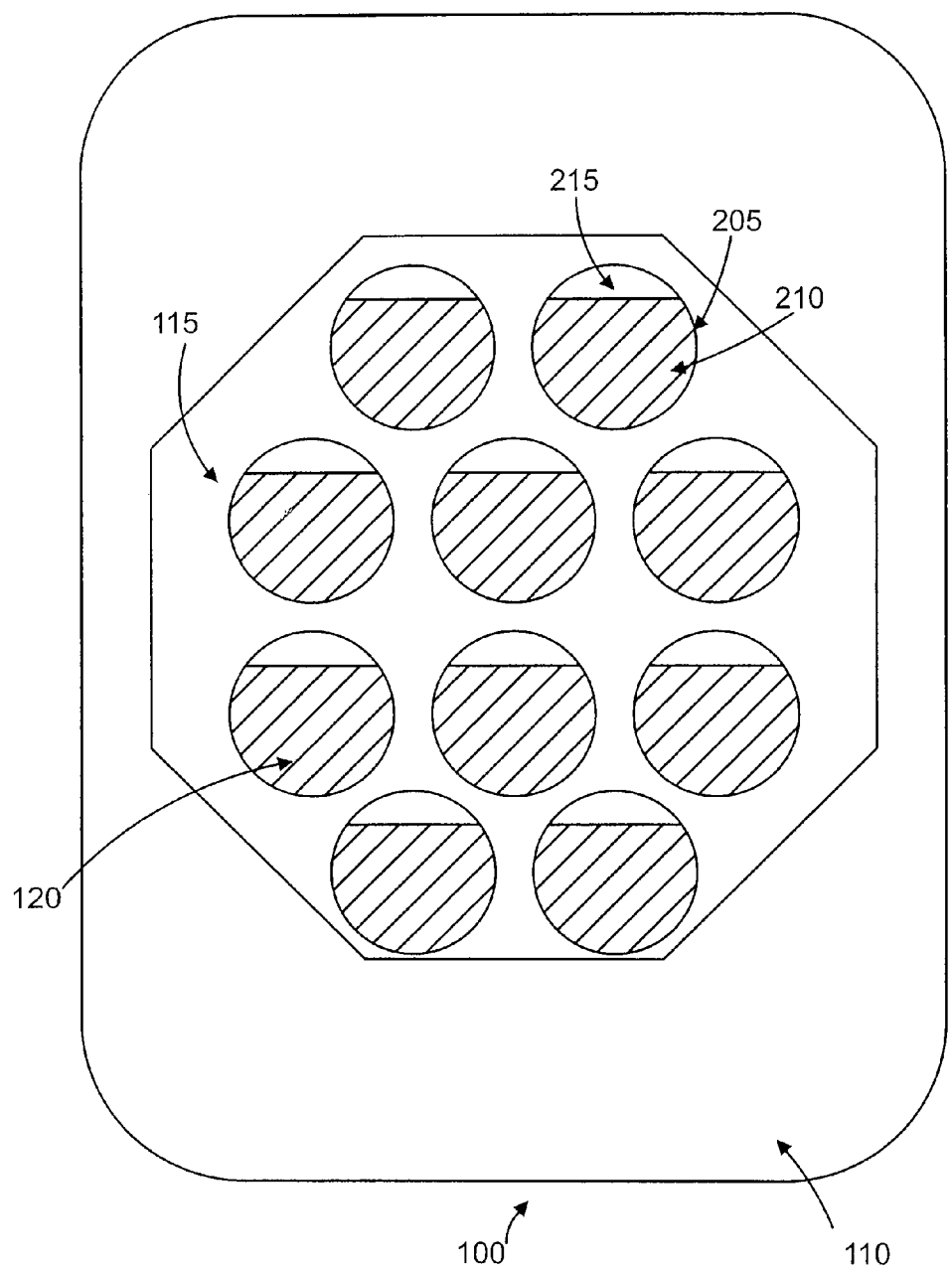
FIG. 2 is a cut-away view showing further detail of the temperature modules shown in FIG. 1.

FIG. 2 shows a cut-away view having greater detail of one embodiment of the therapeutic modules 120. The therapeutic module 120 may include a shell 205 and a therapeutic medium 210 situated within an interior space 215 of the shell 205. The shell 205 may be any shape, for example, substantially spherical, oval, cubic, irregular, etc. In an alternative embodiment, the therapeutic module may be a solid therapeutic medium. In this alternative, the therapeutic medium 210 is a material that has a large heat capacity or undergoes a chemical reaction or solid-solid phase change, for example.

The therapeutic modules 120 may be dimensioned, for example, to be approximately equal in volume or to be two or more different volumes to more densely fill the bag. In one preferred embodiment, each module 120 has a volume less than 0.4 cubic inches. Thus, the therapeutic pack 100 conforms to contours of the area to be subjected to a therapeutic treatment, more effectively promoting uniform application of heating or cooling, for example, as well as reducing the likelihood that the therapeutic pack 100 will slip off the area to be subjected to the therapeutic treatment. Further, since the individual therapeutic modules 120 may be small relative to the bag 110 and move substantially freely to one another, at least some of the therapeutic modules 120 may come to rest in an area of the therapeutic pack 100 adjacent to at least a portion of the area to be subjected to the temperature treatment. In this manner, more of the therapeutic modules 120 may individually contact the portion of a body needing treatment, thereby promoting a more effective treatment.

Figure 3:
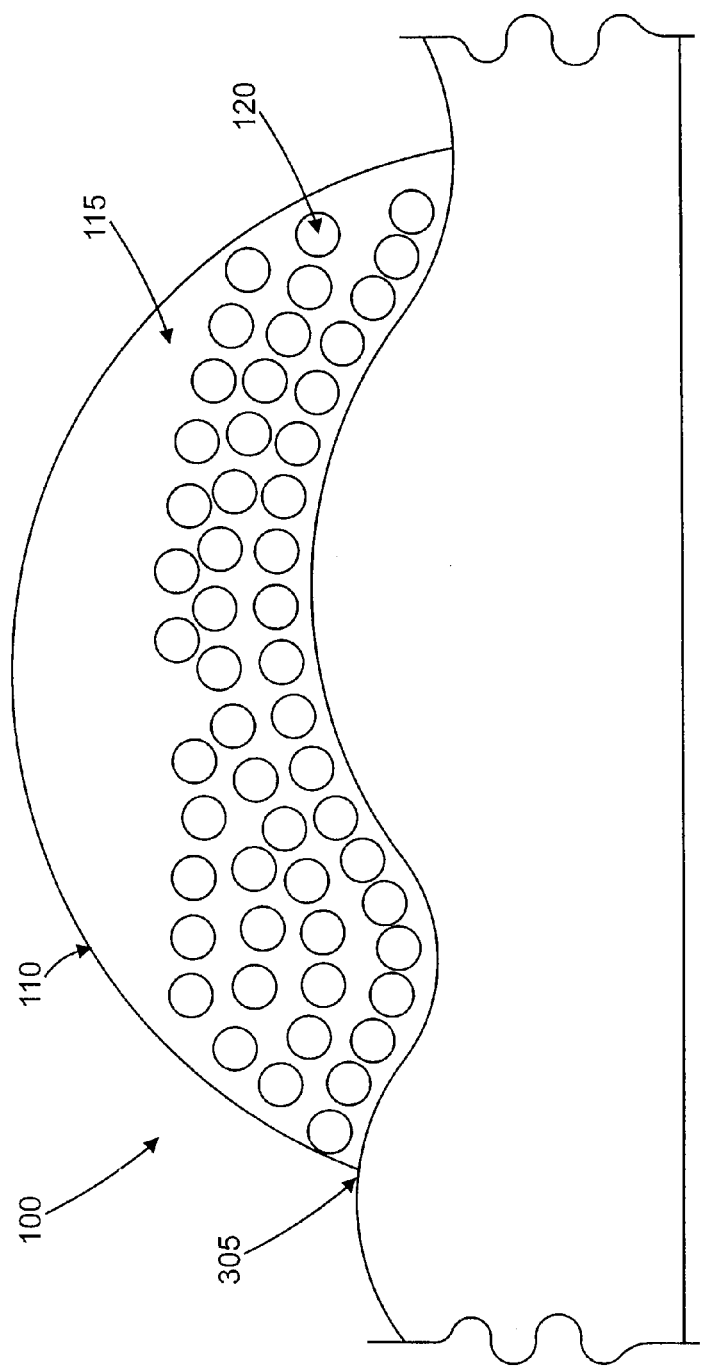
FIG. 3 is a diagram showing application of an exemplary therapeutic pack.

It should be noted that, although FIGS. 1-3 show the therapeutic modules 120 having approximately equal sizes, the therapeutic modules 120 may be of varying sizes and/or shapes, permitting the therapeutic pack 100 to better conform to the contours of the area to be subjected to the temperature treatment and/or better promote the therapeutic effect of the therapeutic pack 100. Furthermore, a volume less than 0.4 cubic inches and/or a diameter of spherical modules less than about 0.5 inches is preferred, because this allows direct contact of the modules with the area to be treated.

The module shell 205 may be of any material operable to contain the therapeutic medium 210, for example, a rigid plastic, a flexible plastic, a sponge-like material, a composite material, an elastomeric material, a non-organic material, an organic material, or a synthetic material may be used. A shell of polyethylene or polypropylene is preferred for encapsulating phase change materials. Polypropylene is preferred for phase change materials having a phase transition of greater than 20° C.

The therapeutic medium 210 may include any material operable to provide a therapeutic treatment to the body such as heat or cold therapy. For example, the therapeutic medium 210 may include a liquid, a solid, and/or a gelatinous material. For example, the therapeutic medium 210 may be a phase change material, such as water, which provides therapeutic cooling to an area of the body during melting from its frozen state to its liquid state. The therapeutic pack 100 may provide repeated therapeutic treatment by refreezing the liquid water, for example, in a freezer compartment. Water is a convenient phase change material, because it undergoes a phase change at 0° C., a temperature easily achieved in an ordinary freezer compartment.

Also, water has a large heat of fusion, which provides prolonged cooling of the area of the body undergoing treatment, and water is non-toxic. Thus, water is safe and effective. Other phase change materials are known that are also safe and effective. For example, PCM are available having a range of phase transition temperatures from −31° C. to 90° C., such as the materials offered by TEAP Energy and other firms.

In addition to or in lieu of a liquid, the temperature medium 210 may include, for example, a chemical cooling or heating agent operable to provide the cooling or heating temperature via a chemical reaction, without the need for being externally cooled or heated.

It should be noted that the interior space 215 of the shell 205 may be completely filled with the temperature medium 210 or, alternatively, only be partially filled with the temperature medium 210. Partially filling the shell 205 with the temperature medium 210 may permit the temperature medium 210, for example, liquid water, to expand within the module container 205 while freezing or heating, without rupturing the shell 205.

It should also be noted that, although FIG. 2 shows the shell 205 filled with the temperature medium 210, the interior space 215 of the module container 205 may alternatively be filled with air or be devoid of any temperature medium 210 whatsoever. Alternatively, the temperature 210 may be a solid that has the same composition as the shell, such as a material with a high heat capacity, creating a solid therapeutic module 120.

Referring now to FIG. 3, there is seen a diagram showing the application of an exemplary therapeutic pack 100 according to the present invention. When applied to an area to be subjected to a cold or heat treatment 305, for example, an injured portion of the human body (e.g., a human knee), the therapeutic modules 120 of the therapeutic pack 100 move substantially freely relative to one another, even if the therapeutic pack 100 is applied immediately after being removed from a cooling source, such as a freezer. In this manner, the therapeutic modules 120 conform to the area to be subjected to a temperature treatment 305, without the need for a subdividing deforming force and without the need, for example, to wait for the therapeutic pack 100 to at least partially thaw.

Further, it is believed that the ability of the therapeutic pack 100 to conform to the area treated 305, helps the therapeutic pack 100 to stay on any area to be treated, for example, the injured portion of the human body. In addition, a bag 110 of a material that drapes under the weight of the therapeutic pack 100 itself allows the therapeutic medium to come to rest adjacent to the entire surface to be treated, including reentrant curvature on the surface, depending on the size and shape of each of the plurality of therapeutic modules 120.

In still another example, a spandex material is used. For example, Lycra,® is a brand name of stretchable fibers used in spandex fabrics in which the fiber-forming substance is a long chain synthetic polymer comprised of at least 85 percent of a segmented polyurethane.[1] For example, the spandex material may be a blend, such as a 82% nylon and 18% spandex tricot material. The blend of nylon spandex tricot allows lengthwise and crosswise stretch in the bag. In addition, the blend allows the bag to conform readily to the complex curves of the human body. The blend also allows the bag to absorb less water than a bag having material made of cotton. Yet another feature of such a bag is that it is very resistant to runs.

Lycra® is a registered trademark of Invista.

In one preferred embodiment, an 82% nylon and 18% spandex tricot fabric is selected having a fabric density of about 200 grams per square meter (200 g/m$^2$). This preferred embodiment provides excellent reusability of the therapeutic bag through a multitude of freeze/thaw cycles, while allowing the material to breath and to drape over an area of the body. Furthermore, the feel of the material on the skin when applied immediately after removal from a freezer is comfortable, avoiding a sensation of freezer shock.

In one embodiment, the module shell is a low density polyethylene.

Alternative combinations and variations of the examples provided will become apparent based on this disclosure. It is not possible to provide specific examples for all of the many possible combinations and variations of the embodiments described, but such combinations and variations may be claims that eventually issue.

What is claimed is:

1. A therapeutic pack for providing therapeutic treatment to an area of a body comprising:
    a fabric bag consisting of a fabric of a taffeta or a spandex, such that the bag drapes; and
    a plurality of therapeutic modules; wherein the therapeutic modules comprise a phase change material encapsulated by a module shell of a polyethylene or polypropylene, each of the plurality of therapeutic modules being enclosed within the bag, the therapeutic modules moving freely within the bag such that at least a plurality of the therapeutic modules directly contact the fabric of the bag as the bag drapes on the area of the body.

2. The therapeutic pack according to claim 1, wherein the bag is made of a nylon taffeta, a polyester taffeta, or a polyester nylon taffeta.

3. The therapeutic pack according to claim 2, wherein the bag consists of a nylon taffeta.

4. The therapeutic pack according to claim 1, wherein the bag consists of a spandex.

5. The therapeutic pack according to claim 4, wherein the bag consists of a spandex tricot.

6. The therapeutic pack according to claim 5, wherein the spandex tricot is a blend of 82% nylon and 18% spandex tricot.

7. The therapeutic pack according to claim 6, wherein a density of about 200 grams/square meter for the blend is selected.

8. The therapeutic pack according to claim 1, wherein the phase change material undergoes a phase transition at a temperature less than 20° C.

9. The therapeutic pack according to claim 1, wherein the phase change material undergoes a phase transition at a temperature greater than 20° C.

10. The therapeutic pack according to claim 9, wherein the plurality of therapeutic modules are microwaveable.

11. The therapeutic pack according to claim 1, wherein the plurality of therapeutic modules are less than one-half inch in diameter.

12. The therapeutic pack according to claim 1, wherein the bag includes a resealable opening, whereby access to the therapeutic modules is provided.

13. The therapeutic pack according to claim 1, wherein the module shell is of a polyethylene.

14. The therapeutic pack according to claim 13, wherein the module shell is of a low density polyethylene.

15. The therapeutic pack according to claim 1, wherein the module shell has an outer diameter of between about 11/32 inches and 13/32 inches.

16. The therapeutic pack according to claim 1, further comprising an antifungal agent or an anti-microbial agent incorporated in the fabric of the bag, the module shell, or both thereof.

17. A therapeutic pack for providing therapeutic treatment to an area of a body comprising:
    a fabric bag consisting of a fabric of a taffeta or a spandex, such that the bag drapes; and
    a plurality of therapeutic modules; wherein the therapeutic modules comprise a phase change material encapsulated by a module shell of a polyethylene or polypropylene, each of the plurality of therapeutic modules being enclosed within the bag, the therapeutic modules moving freely within the bag such that at least a plurality of the therapeutic modules directly contact the fabric of the bag as the bag drapes on the area of the body, wherein an anti-microbial agent is incorporated in the module shell.

* * * * *